United States Patent [19]
Bromley et al.

[11] Patent Number: 5,614,381
[45] Date of Patent: Mar. 25, 1997

[54] METHOD FOR THE INDUCIBLE PRODUCTION OF PROTEINS IN GENETICALLY MODIFIED EUKARYOTIC HOST-CELLS MULTIPLIED IN VIVO

[75] Inventors: Peter Bromley, Chene-Bougertes; Michel Dreano, Vessy, both of Switzerland; Michel Fischbach, Quetigny, France; Xavier Fouillet, Collonges s/Saleve, France; Prudent Padieu, Dijon, France; Richard Voellmy, Miami, Fla.

[73] Assignee: Rothwell Properties Limited, Douglas, Isle of Man

[21] Appl. No.: 421,277

[22] Filed: Apr. 13, 1995

Related U.S. Application Data

[63] Continuation of Ser. No. 197,450, Feb. 16, 1994, abandoned, which is a continuation of Ser. No. 972,713, Nov. 6, 1992, abandoned, which is a continuation of Ser. No. 830,456, Feb. 5, 1992, abandoned, which is a continuation of Ser. No. 228,925, filed as PCT/EP87/00599 Oct. 12, 1987 published as WO88/02778 Apr. 21, 1988, abandoned.

[30] Foreign Application Priority Data

Oct. 15, 1986 [EP] European Pat. Off. .............. 86810455

[51] Int. Cl.$^6$ .............. C12N 15/00; C12N 5/00; C12D 21/06; A01N 63/00
[52] U.S. Cl. .................. 435/69.1; 435/172.3; 424/93.21
[58] Field of Search .............................. 435/172.3, 240.2, 435/69.1; 424/93.21

[56] References Cited

U.S. PATENT DOCUMENTS 4,399,216  8/1983  Axel .
4,537,852  8/1985  Sugimoto et al. ...................... 435/215

OTHER PUBLICATIONS

Activation of heat–shock genes in eukaryotes, H. Pelham, pp. 31–35 see p. 31, col. 1, line 1–p. 32, col. 1, line 1; p. 34, col. 1, line 60–col. 2, line 27; figure 2.
Chemical Abstracts, vol. 107, No. 17, Oct. 26, 1987, (Columbus, Ohio, US)/.
Wurm et al PNAS 83: 5414, 1986.
Carloni et al Gene 31; 49, 1984.
Meneguzzi et al. EMBO J 3: 1365, 1984.
Southern et al J. Mol. Anal. Genet 4: 327, 1982.
Corces et al PNAS 78: 7038, 1981.
Dreano et al, Heat–regulated Expression of the Hepatitis B Virus Surface Antigen in the Human Wish Cell Line, Virus Research, 8 (1987) 43–59.
Simon et al, Selective Induction of Human Heat Shock Gene Transcription by the Adrenovirus E1A Gene Products, Including the 12S E1A Product, Molecular and Cellular Biology, vol. 7, No. 8, Aug. 1987, pp. 2884–2890.
Khandijan et al, Simian Virus 40 and Polyoma Virus Induce Synthesis of Heat Shock Proteins in Permissive Cells, Molecular and Cellular Biology, vol. 3, No. 1, Jan. 1983, pp. 1–8.
Nevins, Joseph R., Induction of the Synthesis of a 70,000 Dalton Mammalian Heat Shock Protein by the Adenovirus E1A Gene Product, Cell, vol. 29, 913–919, Jul. 1982.
Kao et al, Transcriptional Activation and Subsequent Control of the Human Heat Shock Gene During Adenovirus Infection, Molecular and Cellular Biology, vol. 3, No. 11, Nov. 1983, pp. 2058–2065.
Kingston et al, Regulation of Heat Shock Protein 70 Gene Expression by c–myc, Nature, vol. 312, Nov. 15, 1984.
Taylor et al, Stimulation of the Human Heat Shock Protein 70 Promoter In Vitro by Simian Virus 40 Large T Antigen, The Journal of Biological Chemistry, vol. 264, No. 27, Issue of Sep. 25, pp. 16160–16164, 1989.
Pelham, A Regulatory Upstream Promoter Element in the Drosophila Hsp 70 Heat–Shock Gene.
Torok et al, Nucleotide Sequences of Heat Shock Activated Genes in Drosophila Melanogaster. I. Sequences in the Regions of the 5' and 3' ends of the hsp 70 Gene in the Hybrid Plasmid 56H8, vol. 8, No. 14, 1980.
Voellmy et al, Transcription of a Drosophila Heat Shock Gene is Heat–induced in Xenopus Oocytes, Proc. Natl. Acad. Sci. USA, vol. 79, pp. 1776–1780, Mar. 1982.
Voellmy et al, A DNA Segment Isolated from Chromosal Site 67B in D. Melanogaster Contains Four Closely Linked Heat–Shock Genes, pp. 261–270.
Voellmy et al, Isolation and Functional Analysis of a Human 70,000–Dalton Heat Shock Protein Gene Segment, Proc. Natl. Acad. Sci. USA, vol. 82, pp. 4949–4953, Aug. 1985.
Ellwood et al, Differential Regulation of the 70K Heat Shock Gene and Related Genes in *Saccharomyces cerevisiae*, Molecular and Cellular Biology, vol. 4, Aug. 1984, pp. 1454–1459.
Corces et al, Approximate Localization of Sequences Controlling Transcription of a Drosophila Heat–Shock Gene, 1982, pp. 27–34.
Pelham et al, DNA Sequences Required for Transcriptional Regulation of the Drosophila hsp70 Heat–Shock Gene in Monkey Cells and Xenopus Oocytes, 1982, pp. 43–48.
Karch et al, Extensive Regions of Homology in Front of the Two Hsp70 Heat Shock Variant Genes in Drosophila Melanogaster, J. Mol. Biol. (1981) 148, 219–230.
Corces et al, Integration, Transcription, and Control of a Drosophila Heat Shock Gene in Mouse Cells, Proc. Natl. Acad. Sci. USA, vol. 78, No. 11, pp. 7038–7042.

(List continued on next page.)

*Primary Examiner*—Suzanne E. Ziska
*Attorney, Agent, or Firm*—Cushman Darby & Cushman Intellectual Property Group of Pillsbury Madison & Sutro LLP

[57] ABSTRACT

In the production of proteins of biological interest by means of a stress inducible gene expression unit/eukaryotic host cell system, the transformed cell lines are multiplicated by tumour growing in immunodefficient warm-blooded animals, after which the multiplicated cells are cultured in vitro and subjected to stress, whereby expression occurs in high yield. In vivo multiplication rates of $10^5$–$10^6$ the innoculated quantity/2 weeks are reported without any loss of the latent inducible expression capacity.

13 Claims, 8 Drawing Sheets

OTHER PUBLICATIONS

Corces et al, Four Heat Shock Proteins of Drosophila Melanogaster Coded Within a 12–Kilobase Region in Chromosome Subdivision 67B, Proc. Natl. Acad. Sci. USA, vol. 77, No. 9, pp. 5390–5393, Sep. 1980.

Ingolia et al, Sequence of Three Copies of the Gene for the Major Drosophila Heat Shock Induced Protein and Their Flanking Regions, Cell, vol. 21, 669–679,. Oct. 1980.

Hartman et al, Eukaryotic Viral Vectors, Expression of Influenza Virus Hemagglutinin Using SV40 Vectors, pp. 19–27, 1982.

Gething et al, Eukaryotic Viral Vectors, The Expression of the Influenza Virus Hemagglutinin Gene from SV40–HA Recombinants, pp. 29–33, 1982.

Gheysen et al, Eukaryotic Viral Vectors, Expression of Human Fibroblast Interferon $\beta_1$ Gene by Transfection of Monkey Cells with an SV40 Vector, pp. 35–39, 1982.

Pelham et al., A Synthetic Heat–Shock Promoter Element Confers Heat–Inducibility on the Herpes Simplex Virus Thymidine Kinase Gene, The EMBO Journal, vol. 1, No. 11, pp. 1473–1477, 1982.

Kaufman et al, Molecular and Cellular Biology, vol. 2, pp. 1304–1319, Nov. 1982.

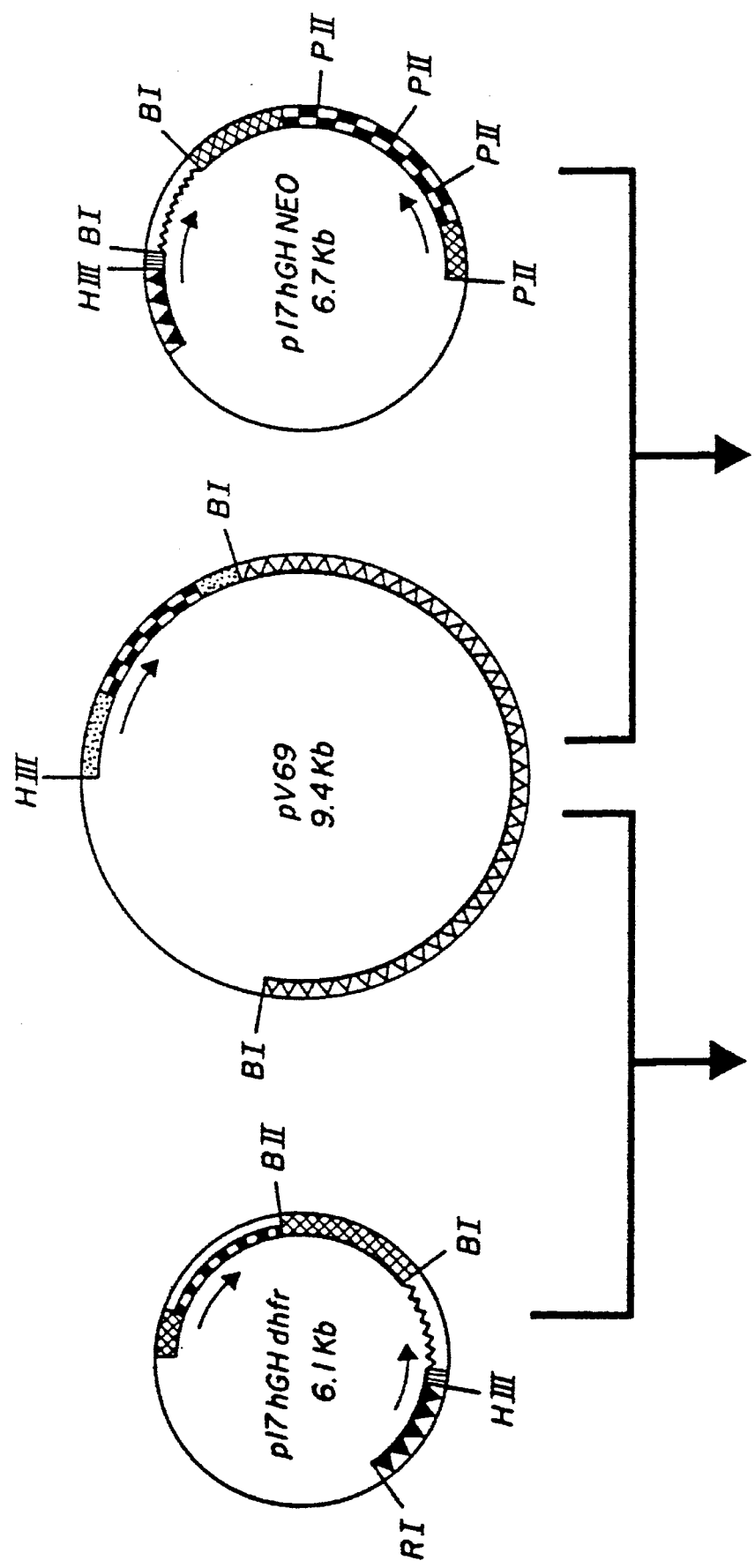

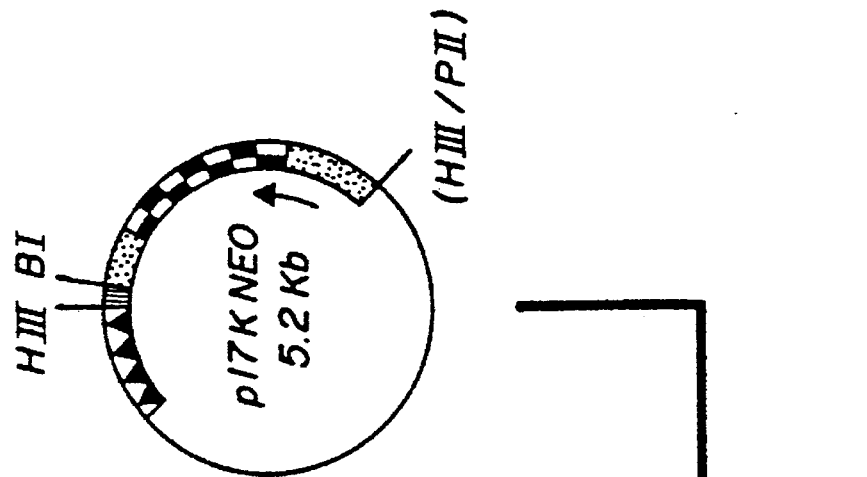
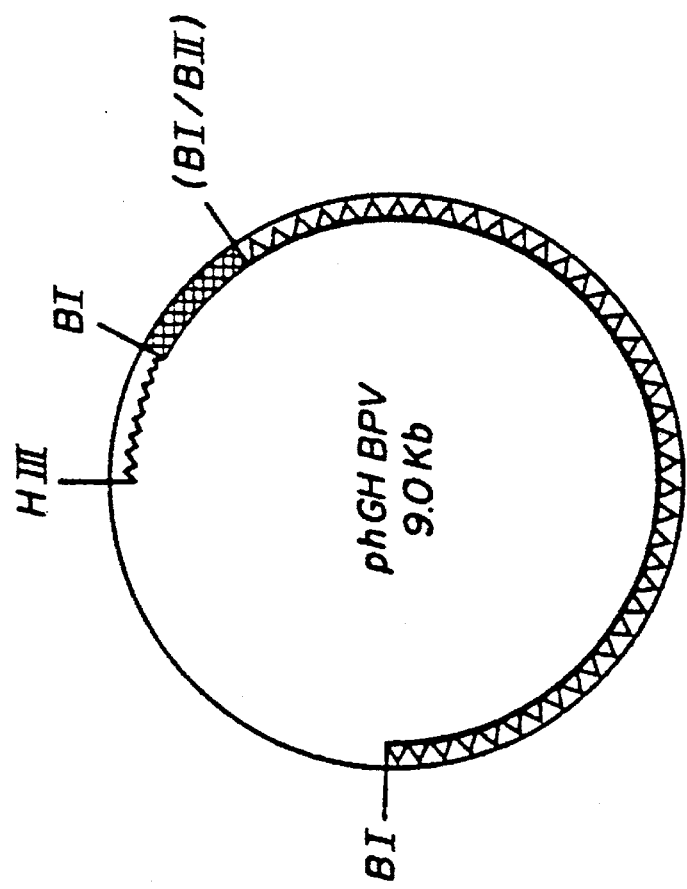

FIG. 10

A KEY TO SEQUENCE SYMBOLS pBR 322 derived sequence pSP 65 polylinker

SV 40 promotor and terminator sequences

Human hsp 70 gene sequence

Human growth hormone gene sequence

Neomycin resistance gene sequence (NEO)

Dihydrofolate reductase gene sequence (dhfr)

Herpes simplex virus thymidine kinase gene sequence

Subgenomic bovine papilloma virus sequence

METHOD FOR THE INDUCIBLE PRODUCTION OF PROTEINS IN GENETICALLY MODIFIED EUKARYOTIC HOST-CELLS MULTIPLIED IN VIVO

This is a continuation of application No. 08/197,450, filed on Feb. 16, 1994, which is now abandoned, which is a continuation of application No. 07/972,713, filed Nov. 6, 1992, now abandoned, which is a continuation of application No. 07/830,456, filed Feb. 5, 1992, now abandoned, which is a continuation of application No. 07/228,925, filed as PCT/EP87/00599 Oct. 12, 1987 published as WO88/02778 Apr. 21, 1988, now abandoned.

The present invention concerns the biochemical production of proteins of interest by the techniques of genetic engineering and, more especially, by inducibly expressing genes of interest in appropriate genetically modified eukaryotic host cells.

The use of and the advantages to inducively expressing genes under the control, for instance, of heat shock expression elements for the production of gene-products of interest in a variety of cell types, have previously been described (see International Applications PCT/EP86/00451 and EP 84 810 066.5; DREANO et al. Gene (1987) 49, 1–8).

Being applied to a eukaryotic expression system, this technique has the intrinsic advantages of having an efficient, general and highly inducible character. These factors are of considerable interest for the commercial production of proteins of biological and pharmaceutical interest, particularly where these proteins are complex, modified, unstable or are potentially toxic to the producer cell. However, their economical performance will rely to a large degree on the use of host/vector models able to ensure a high level of production of fully competent proteins, associated with low cost cell growth and protein purification. For instance, the use of micro organisms as host-cell systems has demonstrated that the ideal quality which should be expected from such a system cannot be found in a single micro organism species, and more appropriate expression systems and vectors are needed. Moreover, most proteins of therapeutic interest are secreted proteins, which frequently require post-translational modifications for activity and immunological specificity, such modifications possibly lacking when translation occurs in bacteria.

Hence, the development of genetically engineered eukaryotic cell lines harbouring recombinant genes constitutes the most promising prospect, despite the relatively primitive state of eukaryotic cell culture technology as compared to that of bacterial systems.

However, although recent developments in tissue culture, employing chemically defined media, constitute an important breakthrough in the adaptation of tissue culture methods to industrial production, there is presently a need of improved culturine means for multiplication and mass culture of cells transformed with genetically engineered gene expression systems.

Some of the major problems associated with mass cultures are:
- to obtain a large number of cells (especially sterility, materials, qualified personnel, space)
- to reduce the cost of production, essentially due to manpower but also of culture media containing fetal calf serum (FCS can represent up to 80% of the total production cost).
- to purify the expected proteins of industrial interest and particularly in the case of secretable proteins, to isolate them from the whole suspension media used for cell culture.

SUMMARY OF THE INVENTION

Thus, in an effort to develop the inducible expression of genes of interest harboured by suitable host cells on an industrial scale, the present inventors have uncovered the method disclosed in annexed claim 1.

Briefly stated, appropriate eukaryotic host cell lines capable of generating tumours when innoculated to immunodeficient animals are transfected with nucleic acid constructions containing at least one gene of interest under the control of a stress inducible promotor. With "normal" cells, a transforming gene, e.g. an oncogene, is also added by co-transfection to impart to the cells unrestricted multiplication capacity. Then the transformed cells which are capable of expressing said gene of interest upon induction are innoculated to immunodeficient animals whereby they are transiently multiplicated in the form of rumours developed by the animals. Surprisingly, and despite the presence in the cells of transcription units not expressed under normal growth conditions, the rates of multiplication were very high (about $10^5$–$10^6$ times the innoculated quantity in 1–2 weeks) without cell degeneracy or loss of the capacity of expressing the gene of interest under stress. This method is also particularly useful for obtaining rapidly and at relatively little expense identification and testing quantities of engineered protein variants of natural proteins.

It should be noted at this stage that the multiplication of certain cell lines by tumoral transplantation in warm-blooded animals is not novel per-se. For instance, GB-A-2,083,826 (HAYASHIBARA) discloses the multiplication of insulin producing, human oncogenic cells by transplantation into warm-blooded animals such as nude mice or immunosuppressed mammals (rats, hamsters, etc.) and birds. However, the types of cell lines involved in this prior art only include easily preservable stable cell lines such as insuloma, lung tissue carcinoma, lymphoblast or hybridoma cells. No corresponding multiplication of cells incorporating genes dominated by heat-shock elements has been previously reported, to the knowledge of the present inventors. Furthermore, the rapid in-vivo multiplications of cells of the type involved here, i.e. containing a recombinant stress-inducible expression system, in very high yield, without the production of undesirable inhibitory products and full preservation of heat-shock inducibility, constitutes a very important technical step vis-a-vis the previous techniques.

In short, the experiments which support the claimed method include the following embodiments:

Genes coding for products of interest (hormones, enzymes and other proteins of interest for diagnoses and pharmaceutical applications) were placed into suitable vectors under the transcriptional and translational control of heat-shock promoter elements of eukariotic origin (human, Drosophila, etc.). Optionally, other precursor or post-translational sequences and variants thereof were also introduced into the nucleic acids of concern, all this being carried out by usual recombinant DNA techniques. Most of this has been disclosed in a previous application (PCT/EP86/00451) incorporated herein by reference.

Then, suitable host cells were transfected with recombinant DNA's including a hybrid gene of interest under control of a hsp 70 sequence and an oncogenic transforming gene. When tumoral host-cells were used, no additional oncogene to promote multiplication was necessary. Contrastingly, when host cells such as NIH-3T3 were used, co-transfection was brought about using an oncogenic transformant sequence of cellular or vital origin. Then, after further in vitro expansion and testing for expression of the gene under heat shock, the transformed cell lines were injected into immunodeficient animals, for instance nude mice or immunodepressed rats and the tumors were allowed to grow to about $10^9$–$10^{10}$ cells.

The tumours were removed, minced and the cells were dissociated, for instance trypsinized, and placed into culture media whereby they could subsequently be stressed. The gene of interest driven by a heat-shock control element, was induced and the cells expressed the protein of interest. The product was then collected by usual means, for example affinity chromatography.

Details on the various embodiments of this invention are found hereafter and in the sub claims. These details will be better understood with reference to the annexed figures, a list of which is summarized below.

BRIEF DESCRIPTION OF THE ANNEXED FIGURES (FIGS. 1–8 AND 11–13 ARE PHOTOGRAPHS)

FIG. 9 represents schematically the construction of plasmid p17HBN. FIG. 9a represents plasmid p17hGH dhfr (Dreano et al. Gene, in press) containing a hsp70-hGH hybrid gene and the mouse dihydrofolate reductase gene under the control of the SV40 early promotor sequence, and terminated by the SV40 terminator sequence.

FIG. 9b represents plasmid pV69 (Meneguzzi et al. 1984, EMBO J. 3; 365–371) containing the neomycin resistance gene under the control of the herpes simplex thymidine kinase promotor and terminator, and the 5.4 kb bovine papilloma virus subgenomic fragment.

FIG. 9c represents plasmid p17hGH NEO (PCT/EP86/00451) containing the hsp70-hGH hybrid gene and the neomycin resistance gene under the control of the SV40 early promotor sequence and terminated by the SV40 terminator sequence.

FIG. 9d represents plasmid phGH BPV which results form the ligation of a HindIII-BamHI fragment derived from p17hGH dhfr and a 7.5 Kb fragment resulting from the digestion of pV69 with HindIII and partial digestion with BamHI.

FIG. 9e represents plasmid p17K NEO which results from the ligation of a 1.8 Kb HindIII-BamHI fragment derived from pV69 (the HindIII extremity has been filled-in with DNA polymerase I (large fragment); and a 3.4 Kb fragment resulting from the digestion of p17hGH NEO with PvuII and BamHI.

Figure 9F:
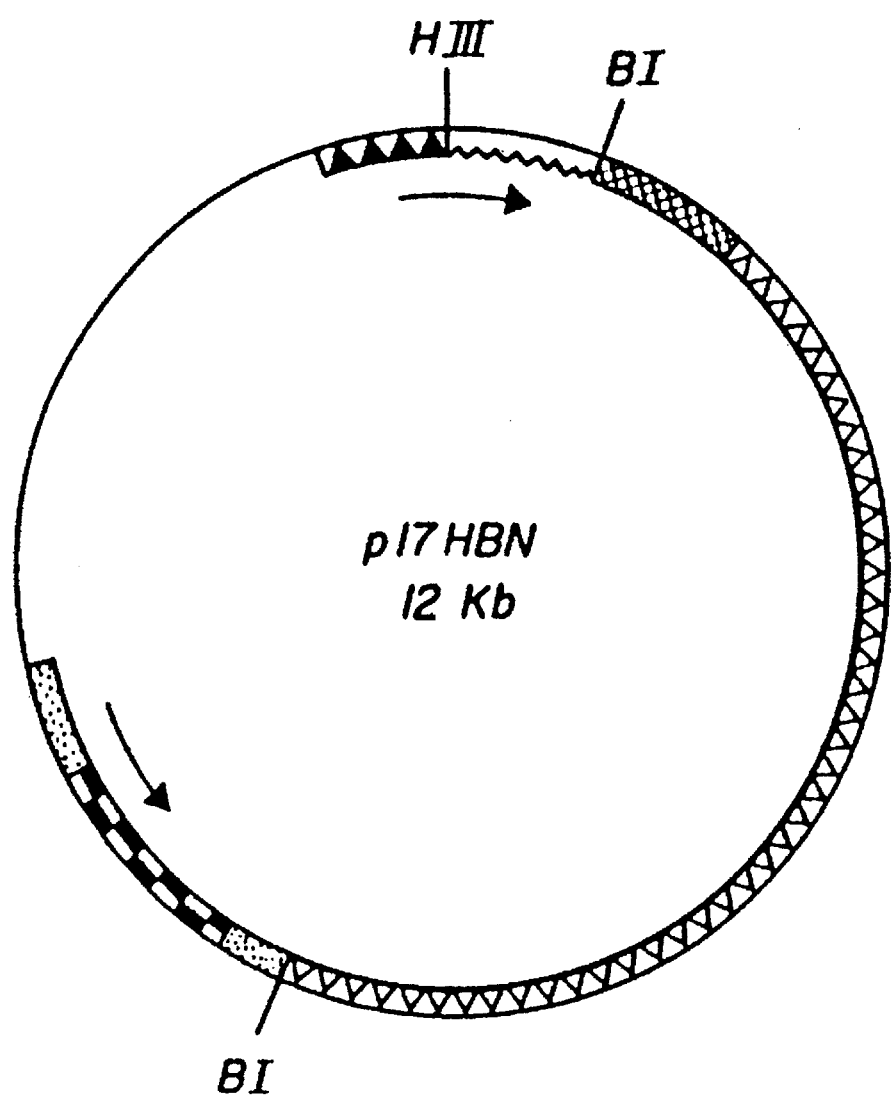

FIG. 9f represents plasmid p17HBN which results from the ligation of a HindIII-BamHI fragment derived from p17K NEO, and a 6.8 Kb fragment resulting from digestion of phGH BPV with HindIII and partial digestion with BamHI.

FIG. 10 is a key to the symbols used in FIG. 9 to define the various DNA sequences involved. The approximate length (in base-pairs) of such sequences in the plasmids schematized in FIG. 9 are given in Table I, below.

Figure 11:

FIG. 11 shows C1.6 tumour cells after dissociation and inoculation in a Petri dish incubated in serum supplemented medium.

Figure 12:
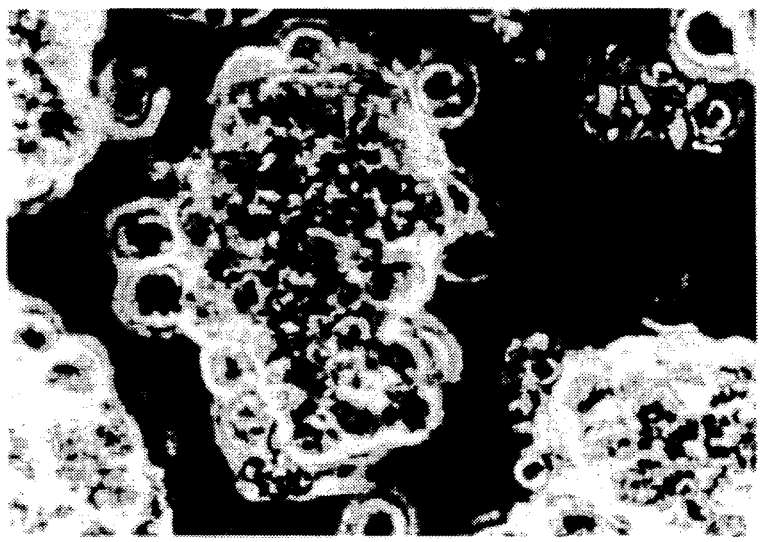

FIG. 12 shows C1.6 tumour cells after dissociation and inoculation in a 1 liter biofermentor with incubation in serum free medium.

Figure 13:
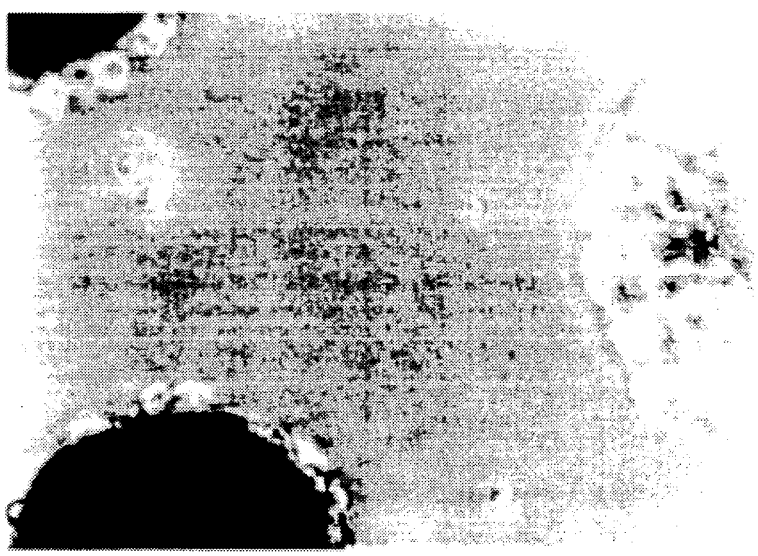

FIG. 13 shows C1.6 tumour cells after dissociation and inoculation in a 2 liter biofermentor with incubation in serum-free medium in the presence of 3 g/l of cytodex 1 microcarriers.

TABLE 1

Identification of the sequences in FIGS. 9a–9f and restriction sites.

| Plasmid | Sequences :kb |
|---|---|
| p17hGH dhfr | D:0.6; B:<0.1; 1:0.7; C:0.7(terminator):0.4(promotor) K:0.7; A:2.3 |
| pV69 | L:0.5(promotor):0:3(terminator) J:1.0; M:5.4:A:2.2 |
| p17hGH NEO | D:0.6; B:<0.1; 1:0.7; C:0.4(promotor):0.7(terminator); J:1.5; A:2.8 |
| phGH BPV | C:0.7(terminator); 1:0.7; M:5.4; A:2.2 |
| p17K NEO | D:0.6; B:<0.1; L:0.5(promotor):0.3(terminator); J:1.0; A:2.8 |
| p17HBN | D:0.6; B:<0.1; 1:0.7 C:0.7(terminator); L:0.5(promotor):0.3(terminator); J:1.0; M:5.4; A:2.8 |

BI: BamHI
BII: Bgl II
HIII: Hind III
PII: PvuII

DETAILED DESCRIPTION OF THE INVENTION

For harbouring the gene recombinant DNA constructions, suitable cell lines had to be selected. Cell lines (NIH3T3) producing high-levels of human growth hormone (hGH) under heat shock control, have been described by Dreano et al., (Gene, (1987) 49, 1–8). In brief, one transformed 3T3 mouse cell line clone 6 (C1.6) can secrete 2 to 5 μg hGH per $10^6$ cells over a 20 hour period following a 2 hours heat shock at 42° C. This concentration is 1200 times the hGH concentration measured in the medium of non heat-treated C1.6 cells. In addition, these cells can be utilized for repeated induction cycles and they were therefore highly suitable for use in the present invention.

We report below the results of transplantation procedures of three genetically engineered mouse cells lines: clone 6 (C1.6), HBN2 and Clone 18 (C1.18). These three cell lines expressed the human hsp70-hGH hybrid gene, and contain the following additional genes; in C1.6, the human Harvey c-ras oncogene (Tabin et al. 1982, Nature, 300; 143–149); in HBN2 the bovine papilloma virus (BPV) subgenomic fragment, and a neomycin resistance gene (used for G418 resistance selection), and in Cl.18 the neomycin resistance gene (Cl.18 is used as a control). Obviously, other genes of interest can also be placed under the control of the hsp70 promotor sequences in similar DNA constructions and expressed similarly. Such genes of interest include for instance vital proteins, hormones, enzymes, blood proteins and others.

Regarding heat-shock control sequences, it is obvious that other heat-shock control elements can be used in place of the sequences mentioned in the specific experiments illustrating the present invention. Genetically engineered variants obtained by nucleotide deletion, mutation and insertion, as disclosed in our application PCT/EP86/00451, are also suitable.

Transplantation of the two first cell lines into nude mice, induced tumour in injected animals. After proteolytic dissociation, or treatment with collagen the tumour cells were able to produce, after heat induction, the same quantity of hGH as the parental cells. Using this methodology we were able to obtain approximatively $10^{10}$ tumour cells per tumour. Finally we showed that these cells retrieved from tumours in animals, can be easily cultivated on cytodex microcarriers in 1 liter or 2 liter bioreactors and, in addition, in chemically defined media serum free medium (SFM), or serum and protein free medium (SPFM) (see CHESSEBEUF and PADIEU., PCT/84/901363.6; FR-A-83/04843). Repeated heat regulated production of hGH was once again obtained.

1. Clone 6

The BALB NIH-3T3 cells (obtained from the ATCC organization) were co-transfected with plasmid p17hGHdhfr, see FIG. 9a, carrying the human growth hormone (hsp70) driven by the human heat shock protein 70 (hsp70) promotor (plasmid p17hGH dhfr is disclosed in PCT/EP86/00451), and by a plasmid carrying the human c-ras oncogene. Two weeks later, foci were isolated, cultured and analyzed for hGH production. Clone 6 was found to secrete 3 μg of hGH per $10^6$ cells in a 15 hour period following a single heat treatment of 2 hours at 42° C.

1.1 Transplantation into nude mice

Spontaneously transformed 3T3 cells injected into nude mice are able to induce tumour formation (Rubin and Arnstein, 1982, Cancer Res., 300; 143–149, Rubin 1984, J. Natl. Cancer Inst., 72, 375–381).

Figure 1:
FIG. 1 shows a nude mouse carrying a sub-cutaneous (s.c.) tumour produced by cell line (C1.6) injection.
Figure 4:
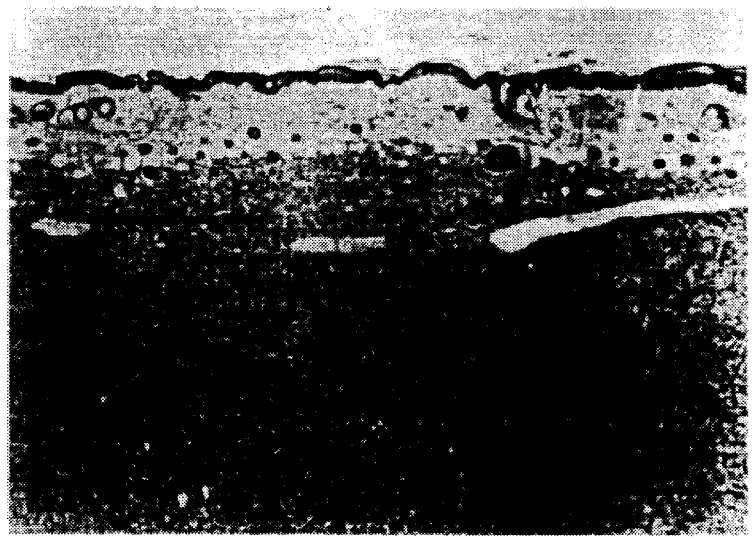
FIG. 4 shows the histological appearance of a s.c. tumour induced by C1.6 cells injection in nude mice.
Figure 5:
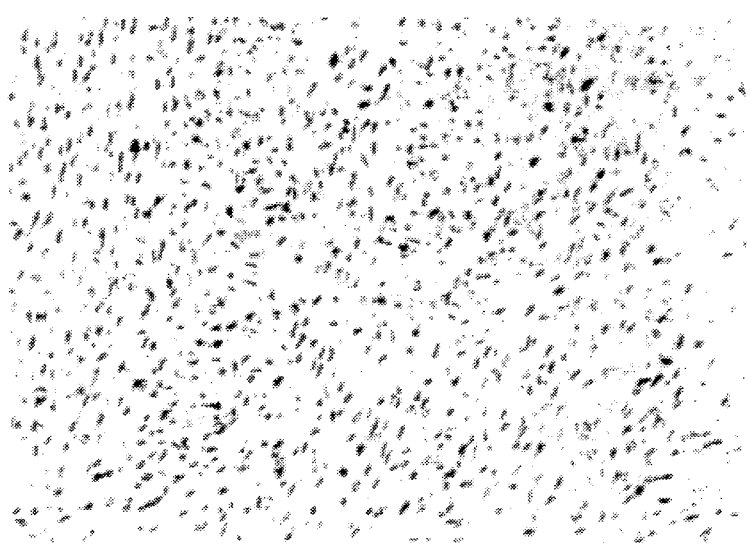
FIG. 5 shows a high magnification of the s.c. tumour shown in FIG. 4. Note the high incidence of mitotic index.
Figure 6:
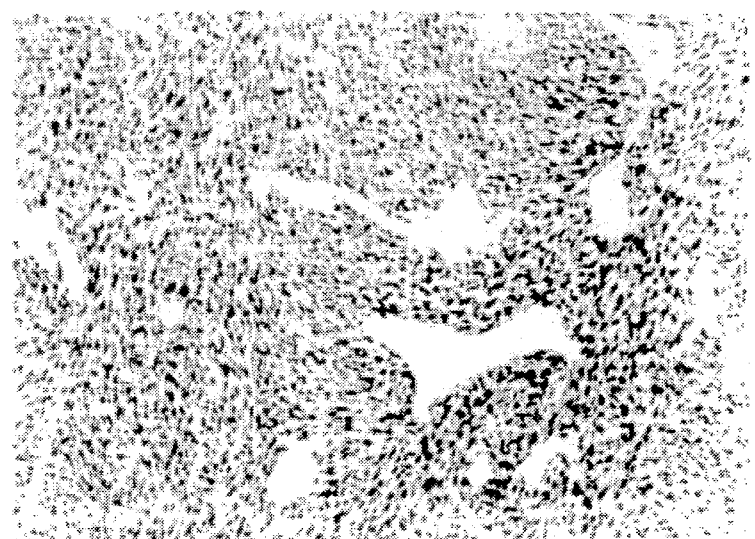
FIG. 6 shows a s.c. tumour induced by C1.6 cells injections in nude mice. Note the vascular spaces.

1.1.1 Subcutaneous transplantation $10^6$ cells in 0.1 ml of culture medium without serum were injected subcutaneously in the dorsal area of nude mice. The first tumour was clearly visible 3 weeks after inoculation (FIG. 1) when the tumour reached a diameter of 20 mm (weighing about 3g), it was dissected. A part of this 1st generation tumour (designated Gl/n) was minced in culture medium and one portion was resuspended to inoculate a monolayer culture for subsequent heat shock, and the other portion was reinjected subcutaneously into other nude mice (to produce G2/n), finally the remaining part of the rumour was fixed with formaldehyde for histological examination. These rumour cells had a great capacity to anchor on plastic dishes. Indeed, 30 min. after seeding in complete medium most of the cells were attached, and presented a fibroblastic aspect. After one night, cells covered the dish and only few dead cells were observed (FIG. 1). After heat treatment of tumour cells (from Gl/n) in cell culture, they were shown to secrete 2.5 to 5 μg of hGH per $10^6$ cells; this is within the same range of production as that of the original Cl.6 cells. In addition, tumour slices (0.5 to 1 g) were found, after heat treatment, to secrete 20 to 100 μg of hGH in suspension medium. Identical experiments were performed in cells from tumours passaged up to 8 times in nude mice (G8/n). Table II (see Experimental part) shows that, with C1.6 the heat regulated production is maintained at a constant rate during 24 generations in nude mice, and the 8 generations in sencar mice; with HBN2, another clone to be described below, a similar result was also observed with cells from the first 2 generations in nude mice. After successive subcutaneous passages into nude mice, the time to tumour onset was reduced to only 2 weeks for the production of a 30 mm tumour, this when the tumour cells came from another nude mouse, compared to the 4 weeks needed to obtain tumours derived from cell cultures. The histological appearance (FIG. 4 to 6) of the subcutaneous tumours remained the same (a fibrosarcoma with a high mitotic index) during passage in nude mice. In the tumours up to a diameter of 30 mm produced in nude mice with C1.6, no major tumour necrosis was observed. Moreover, the periphery of the tumour was well irrigated by blood capillaires (FIG. 6).

1.1.2 Intraperitoneal injection

C1.6 cells, derived from tissue culture ($10^6$ cells), were also injected intraperitoneally into a nude mouse. Three weeks after injection, when a swelling of the abdomen was observed, the mouse was sacrificed. At necrosy, rumours with a marked ascite were noted, and tumour metastases were found in the peritoneal lymph nodes and around the kidneys, as well as in the liver. Microscopically this tumour was similar to the tumours obtained by subcutaneous injection of C1.6 cells.

1.2 Transplantation into sencar mice

Figure 2:
FIG. 2 shows a Sencar mouse (Swiss-derived) with an intramuscular (i.m.) tumour induced by transplantation of C1.6 tumour cells from nude mice.

The Sencar strain of mice (Swiss derived strain, as explained in the experimental section), which is not genetically immunodeficient, was used as a host for genetically engineered transformed cells, as a test of whether these cells can grow in normal mice, after previous passage in nude mice. An attempt to produce tumours in Sencar mice directly from cell cultures was unsuccessful. However, C1.6 cells obtained after a first generation tumour in nude mice. (Gl/n), injected subcutaneously (s.c.) or intraperitoneally (i.p.) into Sencar mice, produced respectively s.c. and j.p. tumours in Sencar mice (denominated Gl/s/sc and Gl/s/ip FIG. 2). This experiment was repeated with a 2nd generation tumour in nude mice (G2/n) which, injected s.c. into a Sencar mouse, also produced an s.c. tumour in Sencar mice. A direct passage of C1.6 tumours from Sencar to Sencar was also successful since an i.p. tumour in Sencar mouse (Gl/s/ip) was transplanted into several other Sencar mice by s.c., i.p. and intramuscular (i.m.) routes, to produce the G2/s tumours. I.m. and s.c. tumours have been observed and Sencar to Sencar transplantations can be continued. The histological structure of the tumours in Sencar mice is similar to that of those induced in the nude mice.

1.3 Transplantation into rats

Figure 3:
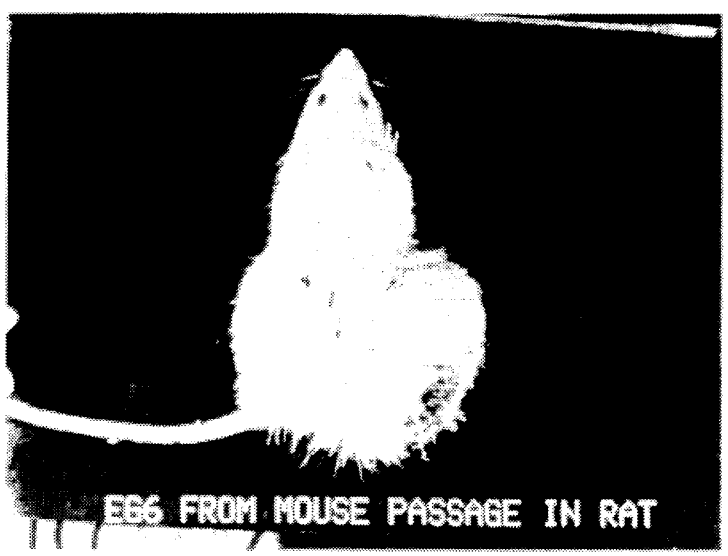
FIG. 3 shows a cyclosporine-immunosuppressed rat with a s.c. tumour induced by transplantation of C1.6 cells from a nude mouse.

In order to verify if interspecies xenografts of genetically engineered, transformed cells could be produced, tumours grown in nude mice (G4/n) were subcutaneously transplanted (pieces of about 75 mm³) into three albino rats. One rat received cyclosporine for immunosuppression (see Experimental part), the two other rats did not received the drug. Two weeks after transplantation, the tumour had regressed in the two normal rats, while a large rumour (12 cm diameter after 3 weeks) was developed in the cyclosporine-immunosuppressed rat (FIG. 3). At necropsy this tumour was found to consist of a large necrotic area surrounded by a layer of about 2 cm of living tumour cells (totalling about 40 g). Its histological structure was once again that of a fibrosarcoma, similar to the tumours induced in mice previously. The heat-induced production of hGH from the cell of this tumour was similar to that from nude mice tumors. Immunosuppressed animals are interesting hosts for growing genetically engineered cells and, in addition to rat, other warm-blooded animals are also usable.

2 Clone HBN 2

HBN2 is also a clone derived from the NIH-3T3 cell line, with incorporation of a plasmid p17HBN, whose construction is described in FIG. 9a–9f, containing 3 transcription units: (1) the hGH gene driven by the human hsp70 promotor, (2) the neomycin resistance gene under control of the herpes simplex virus thymidine kinase promotor (used for cell selection via G418 resistance) and (3) a subgenomic fragment of bovine papilloma virus carrying sequences responsible for the maintenance of multicopy plasmids in a stable form in mouse fibroblasts (Meneguzzi et al. 1984, EMBO J., 3, 365–371).

2.1 Transplantation into nude mice

Two types of transplantation of HBN2 cells from culture (using $10^6$ cells in 0.1 ml of culture medium without serum) were performed. In one case, the cells were injected subcutaneously in the footpad of nude mice. One month later, a growth was noted, this first generation tumour (HBN2/Gl/n) was taken, minced with scissors, and tumour cells were injected into the back of nude mice to produce the second generation tumours (HBN2/G2/n).

Figure 7:
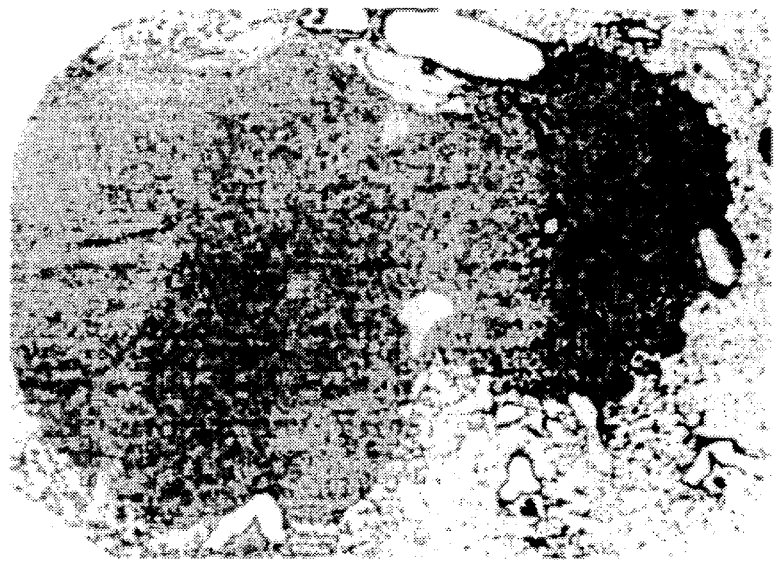
FIG. 7 shows a pulmonary tumour (fibrosarcoma) induced by intratracheal instillation of HBN2 cells in a nude mouse.
Figure 8:
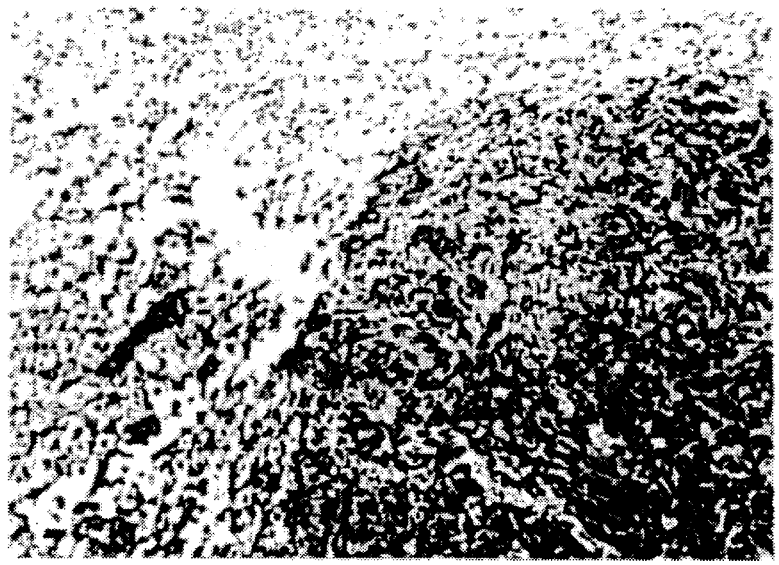
FIG. 8 shows a high magnification of the intrapulmonary tumour shown in FIG. 7.

In the second case, $10^6$ HBN2 cells in 0.5 ml of medium without serum were introduced intra-tracheally into the lungs of a nude mouse. When the animal was necropsied two months later, a large pulmonary tumour (10 mm diameter) invading a pulmonary lobe was found. The tumour (HBN2/Gl/s/it) was assessed microscopically to be a sarcoma (FIG. 7 and 8). Again, cells isolated from tumour derived from clone HBN2 were stable and provided the desired protein in high yield under heat induction in culture medium. (see Table III)

3 Clone 18 (control)

NIH-3T3 cells were co-transfected with plasmid p17hGH dhfr together with a plasmid carrying the neomycin resistance gene under control of the early SV40 promotor (Southern and Berg 1982, J. Mol. Appl. Gen. 1; 327–341). Two weeks later G418-resistant (200 μg per ml of suspension medium) clones were isolated and expanded. Clone 18 was found to secrete approximately 1.5 μg of hGH per $10^6$ cells after heat treatment. Two nude mice were injected s.c. in the foot paw as disclosed above. Three months later no tumour had grown at the injection site which indicated that the transplantation was unsuccessful.

4. Tumour cells grown on petri dishes in serum free media

Tumour cells (C1.6) were dissociated by successive trypsin treatments; one portion from each trypsination step was inoculated on Petri dishes in three different types of media:

serum supplemented medium (SSM) constituted of Williams'E solution plus 5% of fetal calf serum and 5% new born calf serum (see FIG. 11)

serum free medium (SFM) constituted of the Williams'E medium plus 4 g/l of bovine serum albumin, and 7.6 μmole/l of a mixture of 6 free fatty acids (FFA). These six FFA were found indispensable to insure the Krebs cycle functions providing the necessary acetyl-CoA needed in the absence of serum lipids, serum and protein free medium (SPFM) constituted of the Nilliams'E medium and containing 50 mg/l of dextran and 7.6 μmole/l of 6 FFA. After cultivation, the cells were subjected to stress as usual. Results are summarized in Table II (see Experimental part).

The advantages associated with the use of SFM and SPFM are:

(1) Easy selection of a basal synthetic medium for optimal growth or cell function
(2) Reduction of the cost by eliminating the use of fetal calf serum
(3) Use of a defined culture medium which eliminate the many known and unknown components of serum
(4) Supplementation with known amounts of effectors and inhibitors
(5) Simplification of the extraction process especially for secreted proteins such as hGH
(6) Elimination of the extrinsic effects of the serum
(7) Easy formulation and use of a selective media
(8) Elimination of many contaminating substances bound to albumin
(9) Continuation of fundamental research on phenotypic expression of diploid cell line
(10) Innovation in the applied research of new synthetic basal medium which meets the and FDA requirements when normal or recombinant eukaryotic cells are cultured for the production of therapeutic or biologically active molecules for human administration. These advantages are taught by CHESEBEUF and PADIEU N084/03710). After reinoculation on Petri dishes, C1.6 had exactly the same behaviour in SFM and in SPFM as in SSM, i.e. very rapid anchorage, recovering a fibroblastic pattern and complete colonization of the surface of the dish. Tumour cells were similar to the parental C1.6 cells, without any visible contaminating cells. Therefore using SFM and SPFM culture media for cultivating the cells expanded according to the present method were technically and economically advantageous.

5. C1.6 Cells in a biofermentor 5.1 Biofermentator with microcarriers

After each trypsinization step portion of about $3.10^9$ cells were introduced into 3 biofermentators containing respectively 250 ml of one of each of the 3 different media, together with 3 to 5 g/l of cytodex microcarriers. 12 hours after inoculation, the microcarriers were fully covered with tumour cells. Trypan blue coloration indicated the presence of less than 3% of dead cells in any medium (FIG. 13). Cells can be maintained in biofermentors for more than 23 days and are subjected, during this period, to several 4 hrs treatment at 42° C. The production of hGH was noted using an RIA (Radioimmune assay) procedure. Table III (see the experimental part) shows that cells secreted hGH after each heat treatments; the production in SSM was more important than in SFM (see FIG. 12) and even more so than in SPFM.

It is interesting to note that in the SSM biofermentor, about 3 mg of hGH was secreted into the medium. It should be noted that these cells were derived from less than 1 complete tumour, and that a heat treatment could be applied daily.

5.2 Biofermentator without microcarriers

Dissociated tumour cells can also be maintained alive in biofermentator without microcarriers although the conditions there are less favorable. For instance, it was observed that the cells were still alive 5 days after innoculation.

EXPERIMENTAL DETAILS

Method to construct P17HBN (FIG. 9)

Plasmid pBPV hGH : p17hGH dhfr (Dreano et al., ibid) was digested with HindIII, and then partially with BglII. A 1.4 kb fragment containing the human hsp70 promotor, the hGH gene and the SV40 termination signal was extracted from low melting agarose (Sigma, type VII). Plasmid V69 (Meneguzzi et al., ibid) was digested with HindIII and partially with BamHI, a 7.6 kb fragment containing plasmid vector sequences and the 5.4 kb bovine papilloma virus (BPV) subgenomic fragment was isolated and ligated with the above fragment.

Plasmid p17K NEO: pV69 was digested with HindIII, treated with the DNA polymerase large fragment and then digested with BamHI. A 1.8 kb resulting fragment carrying the neomycin resistance gene controlled by the herpes simplex thymidine kinase transcription signals (promotor and terminator), was purified, and ligated to a PvuII BamHI purified fragment from p17hGH NEO containing the human hsp70 promotor and pBR322 derived sequences.

p17HBN: p17K NEO was linearised by digestion with HindIII and BamHI. This fragment including the hsp70 promotor and the neomycin resistance transcription unit, was ligated with a 6.8 kb fragment from pBPV hGH (obtained by total digestion with HindIII and partial digestion with BamHI) containing the hGH gene, SV40 termination signals, and the BPV subgeonomic fragment.

The resulting plasmid p17HBN contains three complete "transcription units":
the human hsp70 -hGH hybrid gene with SV40 terminator
the neomycin resistance gene with TK transcription signals
"the BPV subgenomic fragment"

2. Procedure used to obtain cell lines

2.1 Selection via focus formation

Cells were co-transfected with p17hGH dhfr (Dreano et al. 1986) and pEJ (Tabin et al. 1982, Nature 300, 143–149) using $CaCl_2$ procedure (Graham and van der Eb, 1973, Virol. 52, 456–467). After two weeks, clones that were capable of focus formation were isolated, and expanded. $10^6$ cells of each clone were seeded into 20 $cm^2$ dishes, and after 24 hrs in culture were heat treated for 2 hours at 42° C., and subsequently incubated at 370° C. for 15 hours. Clone 6 produced 3 μg of hGH per $10^6$ cells under these conditions of heat shock.

2.2 G418 Selection

Cells were co-transfected with p17hGH dhfr and pSV2 NEO (Southern and Berg., 1982 J. Mol. Appl.Genet. 1, 327–341), or were transfected with p17HBN using the $CaCl_2$ procedure. After two weeks of culture in complete suspension medium, containing 200 mg of G418 (GIBCO), visible resultant clones were observed after 2 weeks; they were isolated and analyzed further as above. C1.18 and HBN2 were found to inducibly secrete respectively 1.4 and 0.7 μg of hGH per $10^6$ cells.

3 Experiments using mice and rats

3.1 Genetically engineered cell transplantations into nude mice

Nude (nu/nu) mice aged 4 to 6 weeks, from Iffa-Credo (L'Arbresle, France) were housed in Macrolon cages with a cover filter and placed in an air-filtered cabinet. They received an autoclaved diet and normal tap water ad lib.

Portions of $10^6$ genetically modified cells were trypsihated, rinsed twice in Dulbecco's modified Eagle's medium without serum and resuspended in about 0.1 ml of the same medium for intramuscular (i.m.), intra peritoneal (i.p.) and subcutaneous (s.c) injections, and in 0.5 ml for intratracheal instillation.

3.2 Transplantation from nude mice to nude or to sencar mice

Clone 6 cells, s.c. transplanted into nude mice, developed s.c. tumours. When a tumour reached a size of 20 mm in diameter (about 4 weeks after inoculation), the mouse was sacrificed and the tumour (about 3 g) was dissected, minced in culture medium without serum, and a part of the minced tumour (1/10) was reinjected into nude or sencar mice.

Battelle-Geneva breeds the Sencar strain of mice, and albino mouse derived from the Swiss mouse by selection for its sensitivity to skin carcinogens. (Sencar results from "Sensitive to Carcinogens"). Contrary to the nude mice, this strain of mouse is not genetically immunodeprived.

3.3 Transplantation into rats

Pieces of about 75$mm^3$ of a Cl.6 tumour, which was developed in nude mice (4th generation), were transplanted subcutaneously into Sprague Dawley albino rats (IFFA-CREDO, France). The transplantation was performed in 3 rats; 2 normal rats, and one rat chemically immunosuppressed, by ten daily s.c. injection of 60 mg/kg of cyclosporine (Sandoz, Bennet et al., Cancer Res., 45, 4963–4969).

3.4 Histology

When a tumour was taken for retransplantation, a portion was placed into a fixative solution (10% buffered formalin) then processed and sections were stained by haemalin-phloxin-saffron for microscopic observations as described in M. GABE (1968), Techniques Histologiques Ed. Masson et Cie Paris.

4 Detailed method to transfer tumour cells from mice to biofermentors

4.1 Description of the three culture medium

The composition of the three culture media used in this section are:

serum supplemented medium (SSM) constituted of Williams E medium (Gibco) plus 5% of fetal calf serum (FCS) and 5% new born calf serum (both from Boehringer).

serum free medium (SFM) consisting of the same medium, with the addition of 4 g/l of bovine serum albumin (BSA) fraction V (Sigma)(equivalent to 10% FCS) and 7.6 µ mole/l of a mixture of 6 long chain free fatty acids (FFA) in molar proportions close to those of rat plasma (except increased cis-linolenic acid) i e palmitic acid 310%, cis-palmitoleic acid 2.8%, stearic acid 11.6%, cis-oleic acid 13.4%, cis-linoleic acid 35.6%, cis-linolenic acid 5.6% (Sigma).

serum and protein free medium (SPFM) constituted of the same medium containing 50 mg/l of $2.10^6$ dalton dextran (Pharmacia) which was as efficient as 4 g/l BSA to solubilize 7.6 µmole/l of 6 FFA. Each medium contains 50µg/ml of gentamicin (gentalline, Unilabo) as antibiotic.

4.2 Transfer of tumour cells from mice to biofermentors

The mouse was sacrificed, the skin was cut and the tumour easily extracted. After finely mincing with scissors, tumour fragment were transferred to a trypsinization bottle of 50 ml, provided with a magnetic stirrer. To this was added an equal volume of a solution diluted 3 times by trypsin rinsing medium 1:250 (equivalent to trypsin which hydrolyses 250 times its weight of casein) obtained from the Microbiological Associates Company, Bethesda, MID, USA. It was stirred for 10 minutes at 100 rpm, at 37° C., then the suspension of cells was decanted into "Ham F10 medium" cooled on ice (2 volumes of medium per volume of cells) and was centrifuged at 30 g. In parallel, the trypsinization procedure was renewed in the bottle. The sequential digestion with the trypsin was repeated until the dissociation was complete, in general 10 to 13 times. After each centrifugation step, cells were suspended in about 4.3 ml of the culture medium. 1/10 was transferred onto a 20cm² Petri dish (Falcon), and 9/10 into a 1 liter biofermentor (Techne, Cambridge, U.K.). After some trypsination steps trypsin solution was no longer diluted. In another procedure, comparable dissociation was obtained using a collagenase solution (Boehringer, 0.55 g/l).

When the dissociation was complete, suspension medium (SSM, SFP or SPFM, qsp 250 ml) cytodex microcarriers (Pharmacia France, F78340, 3 to 5 g/l) were added. Media are treated with $CO_2$ by bubbling a 5% $CO_2$/air mixture for about 10 min.

Finally, cells are incubated at 37° C. overnight. Media are changed and biofermentors are placed in a 42° C. water bath for 3 or 4 hours followed by a 20 hour period of incubation at 37° C. Media are removed, and replaced with fresh medium before heat treatment or not as described in Table II.

Table II : quantification of hGH produced by C1.6 cells after passage in nude or sencar mice. Tumours were retrieved from mice, minced finely with scissors, and treated with trypsin. Dissociated cells were seeded in 20 cm² Petri dish (Falcon) with $10^6$ cells in 5 ml of Dulbecco's modified Eagle's medium supplemented with 10% fetal calf serum. The next day cells were heat treated for 1 to 2 hours at 705 42° C., or not treated (controls). After 20 hours at 37° C., hGH secreted in sample medium was quantified by means of a hGH RIA kit from Cambridge Inc., Mass. U.S.A. The number in the cell identification code indicate the tumor generation order (see section 1.1.1).

| Mice | Cells | Heat shock (hGH µg/20 ml/$10^6$ cells | control |
|---|---|---|---|
| Nude | C1–6 | 2 to 5 | 0.01 |
| | G1/n | 2 to 5 | — |
| | G2/n | 1.3 | 0.15 |
| | G7/n | 6 | 0.03 |
| | G8/n | 2.5 | 0.03 |
| | G9/n | 2.2 | 0.03 |
| | G11/n | 1.4 | 0.02 |
| | G13/n | 0.7 | 0.01 |
| | G14/n | 1.0 | 0.01 |
| | G16/n | 1.7 | 0 |
| | G18/n | 1.9 | 0.04 |
| | G20/n | 2.9 | 0 |
| | G22/n | 1.2 | 0.0002 |
| | G24/n | 0.7 | 0.0005 |
| Sencar | G2/s | 1.1 | 0.01 |
| | G2/s | 10 | 0.08 |
| | G5/s | >1.3 | 0.04 |
| | G7/s | 4.5 | 0.01 |
| | G8/s | 7.8 | 0.02 |

Table III : hGH secretion in transformed NIH 3T3 cells maintained in a biofermentor. Each biofermentor was seeded with $2.2 \cdot 10^9$ tumour cells in a volume of 250 ml of each of the three culture media described before containing 3 to 5 g/l of cytodex microcarriers. Cells were heat treated, some days after inoculation (see first columm in Table III), for 3 to 4 hours at 42° C. and kept at 37° C. 20 hours afterwards and, finally, put in fresh media. The $CO_2$ concentration in the medium was maintained by bubbling a 5% $CO_2$ in air mixture into the medium. Twelve hours after inoculation, the microcarriers were found to be covered with tumour cells. A trypan blue stain indicated the presence of less than 3% of dead cells in any of the media utilized.

In experiment 2, each biofermentor was seeded with $50.10^6$ tumour cells in a volume of 100 ml of the media shown below containing 2 g/l of citodex microcarriers. The cells were heat treated during 2 h at 43° C., kept at 37° C. for 24 h more, and finally put into fresh media. Suspension media were tested for hGH presence by RIA (provided by Institut Pasteur Production), or ElA.

The cells were maintained in Williams' E medium (experiment 1) or in William's E/HAM F-10 (50:50, v/v) (experiment 2) supplemented with:
SSM; 5% of fetal calf serum and 5% of new born calf serum,
SFM; 4 g/l of bovine serum albumin and 7.6 µmole/l of six FFA (free fatty acids)
SPFM; 50 mg/l of dextran and 7.6 µmole/l of six FFA.

| Days of HS after inoculation | SSM | | SFM | | SPFM | |
|---|---|---|---|---|---|---|
| | mg/l | µg/$10^6$ c | mg/l | µg/$10^6$ c | mg/l | µg/$10^6$ c |
| EXPERIMENT 1 | | | | | | |
| 1 | 0.35 | 0.04 | 0.44 | 0.05 | 0.70 | 0.08 |
| 2 | 0.35 | 0.04 | 0.26 | 0.03 | 0.26 | 0.03 |
| 3 | 1.1 | 0.13 | 0.53 | 0.06 | 0.53 | 0.06 |
| 7 | 2.3 | 0.26 | 1.9 | 0.22 | 0.79 | 0.09 |
| 9 | 2.9 | 0.33 | 1.7 | 0.19 | 0.18 | 0.02 |
| 11 | 2.1 | 0.24 | 1.9 | 0.22 | 0.79 | 0.09 |
| 13 | 4.2 | 0.48 | 0.35 | 0.04 | — | — |
| EXPERIMENT 2 | | | | | | |
| 1 | 0.25 | 0.5 | 0.35 | 0.7 | 0.25 | 0.5 |
| 5 | 2.95 | 5.9 | 0.45 | 0.9 | 0.30 | 0.6 |

-continued

| Days of HS after inoculation | SSM mg/l | SSM µg/10⁶ c | SFM mg/l | SFM µg/10⁶ c | SPFM mg/l | SPFM µg/10⁶ c |
|---|---|---|---|---|---|---|
| 7 | 0.40 | 0.8 | 0.6 | 1.2 | 2.25 | 4.5 |
| 12 | 0.25 | 0.5 | 1.2 | 2.4 | 3.65 | 7.3 |

5. In another series of experiments, a DNA fragment coding for the hepatitis B virus surface antigen (HBsAG) was placed under the control of the human 70 kb heat shock protein promotor. The resulting plasmid construct (p17MS neo carrying a neomycin resistance selection gene) was used in transfection experiments to establish a stable amnion cell line of human origin (Wish), expressing the HBsAg gene in a heat-regulated fashion. Post-translational modifications, such as assembly, glycosylation, secretion and production of both major and middle S proteins appeared to function normally. In addition, the production of HBsAg under various protocols of heat induction was found to be possible. After inoculation into nude mice, development of tumours was observed at the site of injection. Tumour cells, dispersed by means of collagenase or trypsin treatment from excised tumours and subsequently seeded into Petri dishes did secrete the same quantities of HBsAg after heat induction as cells of the original cell line.

Results on the production of the antigen by the tumoral cells are given in Table IV below.

Table IV: HBsAg secreted by WB4 cells before and after passage as tumours into nude mice. Parental cells (around $10^6$) were injected into the back area of nude mice; three weeks later the mice developed tumours. The mice were sacrificed, the tumours were finely minced with scissor and rumour fragments were either injected into nude mice to produce the next generation of tumours, or sequentially treated with trypsin to dissociate tumour cells which were seeded in Petri dishes. Tumour cells at a density of $10^6$ cells per 25 cm² dish were heat treated (HS) or not (Control) for 2 h at 43° C. and post-incubated overnight at 37° C. HBsAg was measured using an ELISA kit obtained from Abbot.

| Generation | WB4 ng HBSsAg/10⁶ cells Control | WB4 ng HBSsAg/10⁶ cells HS |
|---|---|---|
| parental cells | 0 | 80 |
| G1 | 0 | 100 |
| G2 | nd | nd |
| G3 | 0 | 50 |
| G4 | 0 | 38 |

Complete details on the construction of plasmid p17MS neo are published in M. DREANO et al., Virus Research (1987), 8, 43–59.

We claim:

1. A method of producing a protein using an inducible recombinant gene expression unit/host cell system, which method comprises:
   i) introducing into host cells a recombinant DNA molecule containing:
      a) a DNA sequence coding for said protein operably linked to the promoter of a human gene which encodes a 70 kilodalton heat-shock protein (human hsp70 promoter), and
      b) a c-ras oncogene or a subgenomic fragment of bovine papilloma virus;
   ii) inoculating the cells of step (i) into a non-human warm-blooded animal in which said cells of step (i) can multiply, whereby a tumor is formed;
   iii) removing said tumor and effecting dissociation of cells thereof;
   iv) culturing said dissociated cells in a culture medium;
   v) inducing production of the protein by subjecting the cultured cells to a transient heat shock; and
   vi) isolating said protein from the culture medium.

2. A method of producing a protein using an inducible recombinant gene expression unit/host tumor cell system, which method comprises:
   i) introducing into host tumor cells a recombinant DNA molecule containing a DNA sequence coding for said protein operably linked to the promoter of a human gene which encodes a 70 kilodalton heat-shock protein (human hsp70 promoter),
   ii) inoculating the cells of step (i) into a non-human warm-blooded animal in which said cells of step (i) can multiply, whereby a tumor is formed;
   iii) removing said tumor and effecting dissociation of cells thereof;
   iv) culturing said dissociated cells in a culture medium;
   v) inducing production of the protein by subjecting the cultured cells to a transient heat shock; and
   vi) isolating said protein from the culture medium.

3. A method of producing a protein using an inducible recombinant gene expression unit/host cell system, which method comprises:
   i) introducing into host cells a recombinant DNA molecule containing:
      a) a DNA sequence coding for said protein operably linked to the promoter of a human gene which encodes a 70 kilodalton heat-shock protein (human hsp70 promoter), and
      b) a c-ras oncogene or a subgenomic fragment of bovine papilloma virus;
   ii) inoculating the cells of step (i) into a non-human warm-blooded animal in which said cells of step (i) can multiply, whereby a first tumor is formed;
   iii) removing said first tumor and inoculating a portion thereof into an immune competent non-human warm-blooded animal, whereby a second tumor is formed;
   iv) removing said second tumor and effecting dissociation of cells thereof;
   v) culturing said dissociated cells in a culture medium;
   vi) inducing production of the protein by subjecting the cultured cells to a transient heat shock; and
   vii) isolating said protein from the culture medium.

4. The method of claim 2, wherein the DNA sequence coding for the protein is a human growth hormone (hGH) gene or a hepatitis B virus surface antigen (HBsAG) gene.

5. The method of claim 3, wherein the DNA sequence coding for the protein is a human growth hormone (hGH) gene or a hepatitis B virus surface antigen (HBsAG) gene.

6. The method of claim 1, wherein the DNA sequence coding for the protein is a human growth hormone (hGH) gene or a hepatitis B virus surface antigen (HBsAG) gene.

7. The method of claim 1, wherein said recombinant DNA molecule is introduced into said host cells by transfection with plasmid p17HBN carrying an hGH gene under control of said human hsp70 promoter, a neomycin resistance gene driven by a herpes simplex virus thymidine kinase promoter and the subgenomic fragment of bovine papilloma virus.

8. The method of claim 1, wherein said recombinant DNA molecule is introduced into said host cells by co-transfection with plasmid p17 hGH dhfr carrying an hGH gene driven by the human hsp70.promoter and plasmid pEJ.

9. The method of claim 2, wherein the recombinant DNA molecule is introduced into said host cells by co-transfection with plasmid p17hGH dhfr carrying an hGH gene driven by said human hsp70 promoter and plasmid pSV2NEO carrying a neomycin resistance gene under control of a Simian Virus 40 early promoter.

10. The method of claim 1, wherein the host cells are selected from the group consisting of BALB, NIH-3T3 and WISH cells.

11. The method of claim 1, wherein the non-human warm-blooded animal is a nude mouse or a chemically immunosuppressed non-human warm-blooded animal.

12. The method claim 1, wherein said dissociated cells are cultured in a culture medium selected from the group consisting of serum supplemented medium, serum free medium supplemented with fatty acids and serum and protein free medium supplemented with fatty acids and dextran.

13. The method of claim 12, wherein said dissociated cells are cultured in a fermentator in the presence of homogeneously distributed microcarriers or hollow fiber culture system.

* * * * *